United States Patent [19]
Bellussi et al.

[11] Patent Number: 5,888,471
[45] Date of Patent: *Mar. 30, 1999

[54] SYNTHETIC CRYSTALLINE POROUS MATERIAL CONTAINING OXIDES OF SILICON, TITANIUM AND GALLIUM

[75] Inventors: Giuseppe Bellussi, Piacenza; Mario Gabriele Clerici, Milan; Angela Carati; Antonio Esposito, both of Milan, all of Italy

[73] Assignees: Eniricerche S.p.A., Milan; Enichem Synthesis S.p.A., Palermo; Snamprogetti, Milan, all of Italy

[ * ] Notice: This patent issued on a continued prosecution application filed under 37 CFR 1.53(d), and is subject to the twenty year patent term provisions of 35 U.S.C. 154(a)(2).

[21] Appl. No.: 738,734

[22] Filed: Oct. 28, 1996

Related U.S. Application Data

[63] Continuation of Ser. No. 814,191, Dec. 20, 1991, abandoned, which is a continuation of Ser. No. 660,249, Feb. 22, 1991, abandoned, which is a continuation of Ser. No. 532,181, Jun. 1, 1990, abandoned, which is a continuation of Ser. No. 110,926, Oct. 20, 1987, abandoned.

[30] Foreign Application Priority Data

Oct. 22, 1986 [IT] Italy ................................... 22070A/86

[51] Int. Cl.⁶ .................................................. C01B 39/40
[52] U.S. Cl. .......................... 423/705; 423/707; 423/713; 423/DIG. 22; 502/67; 502/77
[58] Field of Search .................... 423/701, 705, 423/707, 713, DIG. 22; 502/61, 77

[56] References Cited

U.S. PATENT DOCUMENTS

| | | | |
|---|---|---|---|
| 3,702,886 | 11/1972 | Argauer et al. | 423/326 |
| 4,410,501 | 10/1983 | Taramasso et al. | 423/326 |
| 4,585,641 | 4/1986 | Barri et al. | 423/326 |
| 4,623,530 | 11/1986 | Cullo et al. | 423/328 |
| 4,639,358 | 1/1987 | Derouane et al. | 423/326 |
| 4,640,829 | 2/1987 | Rubin | 423/328 |
| 4,729,979 | 3/1988 | Zletz | 502/202 |
| 5,246,690 | 9/1993 | Bellussi et al. | 423/DIG. 22 |
| 5,365,002 | 11/1994 | Wallau et al. | 423/DIG. 22 |
| 5,371,307 | 12/1994 | Guth et al. | 423/705 |

FOREIGN PATENT DOCUMENTS

| | | |
|---|---|---|
| 0107876 | 5/1984 | European Pat. Off. . |
| 3237389 | 4/1983 | Germany . |

*Primary Examiner*—Karl Group
*Assistant Examiner*—David Sample
*Attorney, Agent, or Firm*—Hedman, Gibson & Costigan, P.C.

[57] ABSTRACT

A synthetic, crystalline, porous material is disclosed, together with the related preparation process. Such material of zeolitic nature containing oxides of silicon, titanium and gallium corresponds, in the calcined and anhydrous state, to the following empyrical formula:

$$pHGaO_2.qTiO_2.SiO_2,$$

wherein p has a value greater than zero and smaller than or equal to 0.050, and q has a value greater than zero and smaller than or equal to 0.025, and the $H^+$ of $HGaO_2$ can be at least partially replaceable or replaced by cations.

15 Claims, 3 Drawing Sheets

SYNTHETIC CRYSTALLINE POROUS MATERIAL CONTAINING OXIDES OF SILICON, TITANIUM AND GALLIUM

This application is a continuation of application Ser. No. 07/814,191, filed Dec. 20, 1991, now abandoned, which is a continuation of application Ser. No. 07/660,249, filed Feb. 22, 1991, now abandoned, which is a continuation of application Ser. No. 07/532,181, filed Jun. 1, 1990, now abandoned, which is a continuation of application Ser. No. 07/110,926, filed Oct. 20, 1987, now abandoned.

The present invention relates to a synthetic material containing silicon, titanium and gallium oxides, having a porous, crystalline structure of zeolitic nature, and to the process for producing said material.

Such material is structurally similar to zeolite ZSM-5 disclosed in U.S. Pat. No. 3,702,886, formally constituted, in its calcined and anhydrous form, by $M_{2/n}O$, $SiO_2$, $Al_2O_3$ (wherein M=a cation of valence n).

Other synthetic materials structurally correlated to zeolite ZSM-5 are known, such as that disclosed in U.S. Pat. No. 4,061,724, formally constituted, in its calcined and anhydrous form, by $SiO_2$ and that disclosed in BE-886,812, formally constituted, in its calcined and anhydrous form, by $SiO_2$ and $TiO_2$.

We have found now a novel synthetic zeolite, which we'll call as titanium-gallium-silicalite, structurally similar to silicalite, which can be used either as a molecular sieve, or as an ion-exchange material, or as a catalyst in the following reactions: cracking, selectoforming, hydrogenations and dehydrogenations, oligomerizations, alkylations, isomerizations, water removal from oxygen-containing organic compounds, selective oxidations and hydroxylations of organic substrates with $H_2O_2$ (e.g., oxidation of olefins, diolefins, alcohols, hydroxylations of aromatics, etc.).

The synthetic, crystalline, porous material of zeolitic nature of the present invention, containing oxides of silicon, titanium and gallium, meets, in its calcined and anhydrous state, the following empirical formula:

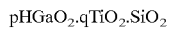

$pHGaO_2.qTiO_2.SiO_2$ wherein p has a value larger than zero and smaller than or equal to 0.050, and q has a value larger than zero and smaller than or equal to 0.025; and the $H^+$ of $HGaO_2$ can be at least partially replaceable, or replaced, by cations.

The passage from a cationic form to another cationic form can be carried out with the usual exchange processes known from the prior art.

The synthetic material in accordance with the present invention results crystalline when tested by X-ray examination.

Such examination was carried out by powder-diffractometer equipped with an electronic pulse counting system, using the CuK-alpha radiation. To compute the intensity values, the heights of the peaks were measured, and referred, as a percentage, to the most intense peak.

The main reflections for the calcined and anhydrous product are characterized by the following values of d (wherein d is the interplanar distance):

| d (Å) | Relative Intensity |
| --- | --- |
| 11.14 ± 0.10 | vs |
| 9.99 ± 0.10 | s |
| 9.74 ± 0.10 | m |
| 6.36 ± 0.07 | mw |
| 5.99 ± 0.07 | mw |
| 4.26 ± 0.05 | mw |
| 3.86 ± 0.04 | s |
| 3.82 ± 0.04 | s |
| 3.75 ± 0.04 | s |
| 3.72 ± 0.04 | s |
| 3.65 ± 0.04 | m |
| 3.05 ± 0.02 | mw |
| 2.99 ± 0.02 | mw |

(wherein vs=very strong; s=strong; m=medium,; mw=medium-weak).

Such a diffraction spectrum is essentially similar to that of ZSM-5, and, consequently, to the other zeolites which are structurally correlated to ZSM-5, which have been mentioned at the beginning of the present disclosure.

The material of the present invention shows an I.R. spectrum characterized by the following most representative values of wn (wherein wn is the wave number):

| wn (cm$^{-1}$) | Relative Intensity |
| --- | --- |
| 1220–1230 | w |
| 1080–1110 | s |
| 965–975 | mw |
| 795–805 | mw |
| 550–560 | m |
| 450–470 | ms |

(wherein s=strong; ms=medium-strong; m=medium; mw=medium-weak; w=weak).

In FIG. 1, the I.R. spectrum is reported, wherein on the abscissa the wave number as cm$^{-1}$ and on the ordinate the percent transmittance are reported.

Such I.R. spectrum is essentially similar to that of the zeolite disclosed in BE-886,812, and is considerably different from that of ZSM-5 (or from similar structures), shown in FIG. 2.

One can observe that in the spectrum the band at 965–975 cm$^{-1}$, characteristic of the titanium-silicalite of BE-886,812 and of titanium-gallium-silicalite is absent.

Summing-up, the herein disclosed material is different from ZSM-5 of U.S. Pat. No. 3,702,886, both due to its empirical formula, and due to its I.R. spectrum, and is different from the zeolite of BE-886,812 due to its empirical formula.

Furthermore, the use of the material of the present invention as a catalyst in the above listed reactions is a further confirmation of the difference of our product relatively to those known from the prior art.

In fact, ZSM-5 of U.S. Pat. No. 3,702,886 is used as a catalyst in such reactions as water removals from oxygen-containing organic compounds, cracking, selectoforming, hydrogenations and dehydrogenations, oligomerizations, alkylations, isomerizations, but results inactive in the reactions between organic substrates and $H_2O_2$ (hydroxylation of phenol to diphenols, oxidation of olefins, etc.), whilst the zeolite of BE-886,812 results to be inactive in the first reactions and active in the last reactions; on the contrary, the herein disclosed zeolite is active in all of the above cited reactions.

A second object of the present invention is the process of preparation for obtaining the above disclosed synthetic, crystalline, porous material.

Said process is characterized in that under hydrothermal conditions a silicon derivative, a titanium derivative, a gallium derivative and a nitrogenous organic base are reacted, with a $SiO_2/Ga_2O_3$ molar ratio of the reactants larger than 100, preferably comprised within the range of from 150 to 600, an $SiO_2/TiO_2$ molar ratio of the reactants larger than 5, preferably comprised within the range of from 15 to 25; an $H_2O/SiO_2$ molar ratio of the reactants preferably comprised within the range of from 10 to 100, more preferably comprised within the range of from 30 to 50, possibly in the presence of one or more alkali- and or alkali-earth-metal salts and/or hydroxides, with a molar $M/SiO_2$ ratio (wherein M is the alkali- and/or alkali-earth-metal cation) of the reactants smaller than 0.1, preferably smaller than 0.01, or equal to zero.

In the empirical formula of the material, gallium has been shown in $HGaO_2$ form, to underline that the material is in $H^+$ form. When the ratios between the various reactants are discussed, for gallium $Ga_2O_3$ form is used, in that it is more usual.

The silicon derivative is selected from silica gel, silica sol and alkylsilicates, among which tetraethyl-silicate is the most preferred; the titanium derivative is selected from titanium salts, such as, e.g., titanium halides, and organic titanium derivatives, such as, e.g., alkyl-titanates, preferably tetraethyl-titanate; the gallium derivative is selected from its salts, such as, e.g., gallium halides, nitrates and hydroxides.

The nitrogenous organic base can be an alkyl-ammonium hydroxide, preferably tetrapropyl-ammonium hydroxide.

In case tetrapropyl-ammonium hydroxide is used, the $TPA^+/SiO_2$ ratio (wherein TPA=tetrapropyl-ammonium) of the reactants is comprised within the range of from 0.1 to 1, preferably of from 0.2 to 0.4. The reactants are reacted by operating at a temperature comprised within the range of from 100° to 200° C. At a pH comprised within the range of from 9 to 14, preferably of from 10 to 12, and for a time ranging from 1 hour to 5 days.

According to another form of practical embodiment of the present invention, titanium-gallium-silicalite can be in the form bonded with amorphous oligomeric silica, with an amorphous oligomeric silica/titanium-gallium-silicalite molar ratio comprised within the range of from 0.05 to 0.2, wherein the titanium-gallium-silicalite crystals are linked by Si—O—Si bridges, the mass of crystals of titanium-gallium-silicalite with silica being in the form of microspheres having a diameter comprised within the range of from 5 to 1000 μm.

The process for preparing the catalyst with the bonding agent is based on the use of an aqueous solution of silica and tetraalkyl-ammonium hydroxide, obtained by hydrolysing a tetraalkyl-silicate, preferably tetraethyl-orthosilicate, in an aqueous solution of tetraalkyl-ammonium hydroxide.

The alkyl radicals in the tetraalkyl-ammonium moiety contain a number of C atoms comprised within the range of from 1 to 5.

The hydrolysis is carried out in the liquid phase at a temperature comprised within the range of from room temperature to 200° C., and preferably within a time of from 0.2 to 10 hours.

In such a solution, silica is in an oligomeric form, and at high enough pH values, i.e., at a pH $\geq 10$.

When crystalline titanium-gallium-silicalite with very fine crystals is dispersed in this solution, the crystal surface is partly attacked by the alkalinity of the medium: such situation favours the formation of stable chemical bonds between the surface of the crystals and the oligomeric silicates in solution. By rapidly drying this suspension, by means of a spray-dryer, water is removed, and at the same time the crosslinking occurs of the oligomers, leading to the obtainment of microspheres formed by a tridimensional lattice wherein the zeolite crystallites are strictly linked by Si—O—Si bridges.

Before being used, the microspheres are calcined first under an inert medium ($H_2$, $N_2$, etc.), then they are oxidated at a temperature comprised within the range of from 150° to 700° C., preferably of from 500° to 600° C.

The optimum concentration of total solids ($SiO_2$, titanium-gallium-silicalite, TAA—OH) of the suspension to be atomized is of from 10% to 40% by weight. By varying the concentration of the solids in the suspension, or the dimensions of the atomizer, the average diameter of the obtained particles can be varied. The diameter of the catalyst microspheres can be thus varied within the range of from 5 to 1000 μm, with the most suitable dimensions for any particular desired application being selected.

In order to better illustrate the meaning of the present invention, some preparation and application examples are hereunder reported, which anyway have not to be understood as being limitative of the same invention.

EXAMPLE 1

6.1 g of $Ga(NO_3)_3.8H_2O$ is dissolved in 70 g of $C_2H_5OH$ and the so-obtained solution is added, with mild stirring, to a solution constituted by 22.7 g of tetraethyl-titanate and 416 g of tetraethyl-silicate.

The so-obtained clear alcoholic solution is added, with moderate stirring, to 870 g of an aqueous solution at 14% of tetrapropyl-ammonium hydroxide. The mixture is maintained stirred, while being possibly heated, until a single-phase, clear solution is obtained. Then, 700 g is added of demineralized water, with the mixture being stirred for a further hour. The obtained mixture is then charged to a stirred stainless-steel autoclave, and is heated, under its autogenous pressure, up to the temperature of 170° C. These conditions are maintained for 15 hours, the autoclave is then cooled and the reaction mixture is discharged. The obtained suspension is centrifuged and the solid is washed by re-dispersion and centrifuging, is dried at 120° C. and is then calcined at 550° C. for 4 hours.

The obtained product is then exchanged by the known processes into the protonic form.

The chemical analysis shows that the anhydrous product has the following composition;

$SiO_2/Ga_2O_3=195.5$;

$SiO_2/TiO_2=54.2$.

Figure 1:
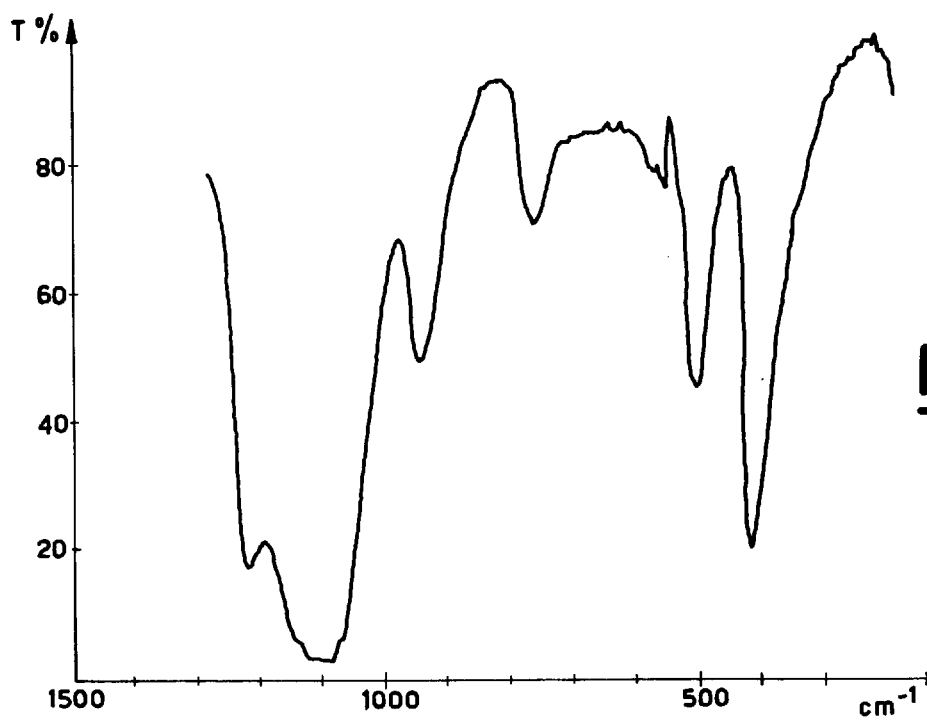
FIG. 1 is an IR spectrum of the crystalline porous material of the present invention.
Figure 2:
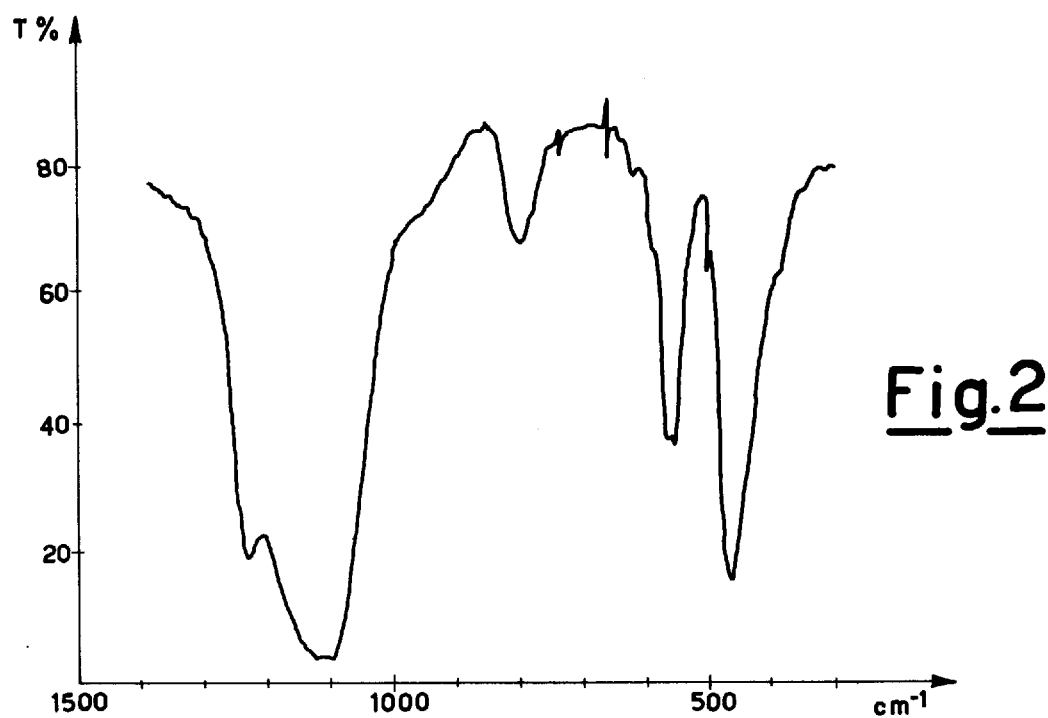
FIG. 2 is an IR spectrum of titanium silicate according to the prior art.
Figure 3:
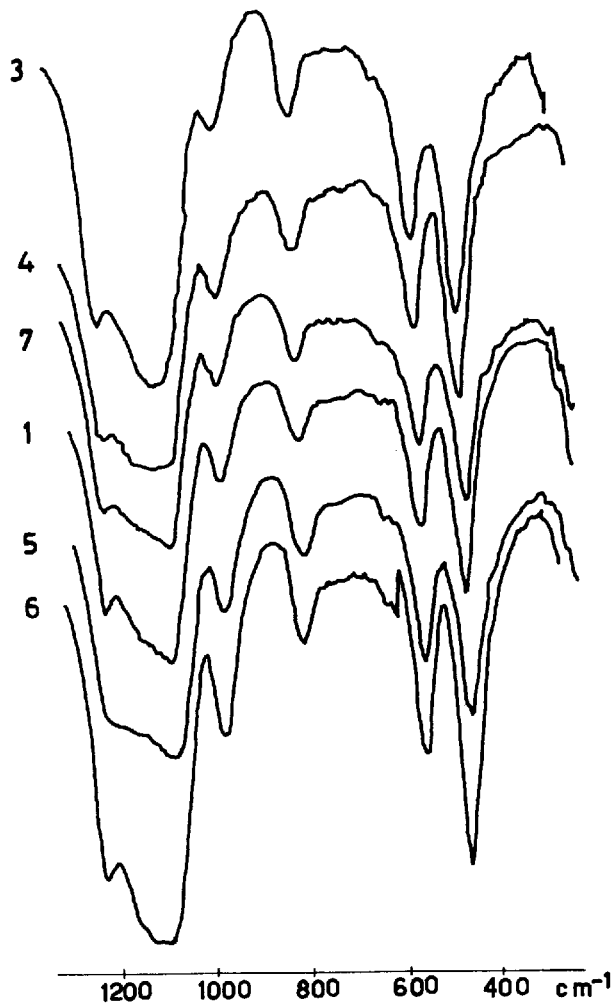
FIG. 3 is an IR spectra of the products of Examples 2 to 6.

The powder X-ray diffraction analysis shows that the product is crystalline, and has a ZSM-5-type structure. The I.R. spectrum thereof is shown in FIG. 3.

EXAMPLES 2–6

By the same modalities as of Example 1, five preparations are carried out, for which the molar compositions of the reactant mixtures and of the obtained products, as they result from the chemical analysis, are reported in Table 1.

In the Examples 3 and 6 crystallization times and temperatures have been modified. Particularly in Example 3 crystallization has been effected in 3 hours at 190° C. and in Example 6 in 5 days at 100° C.

The reaction mixture prepared as disclosed in Example 2 under the described conditions does not crystallyze, but it remains as an amorphous product having a jelly consistency.

The products from Examples 3 through 6 are crystalline and the X-ray diffraction analysis shows that they are structures of ZSM-5 type.

The I.R. spectra are shown in FIG. 3.

EXAMPLE 7

By the same modalities as of Example 1, a reaction mixture is prepared, which has the following molar ratios:

$SiO_2/TiO_2=20$;
$SiO_2/Ga_2O_3=200$;
$TPA^+/SiO_2=0.3$;
$H_2O/SiO_2=40$.

The only difference consists in that gallium nitrate is directly dissolved in the solution at 14% of tetrapropyl-ammonium hydroxide, and not in ethyl alcohol. The reaction mixture is charged to the autoclave, and is left standing at 15 hours at 170° C. under its autogenous pressure. The discharged product is centrifuged and washed twice by re-dispersion and centrifugation, it is then dried one hour at 120° C. and is then calcined 4 hours at 550° C. in air.

The product obtained in the calcined and anhydrous form has the following chemical composition:

$SiO_2/TiO_2=38.2$;
$SiO_2/Ga_2O_3=140$.

The powder X-ray diffraction analysis shows the presence of a crystalline structure of ZSM-5 type, and of traces of crystalline $TiO_2$ (anatase).

In FIG. 3, the I.R. spectra are reported of the gallium-titanium-silicalites of Examples 1 and 3 through 7.

Figure 4:
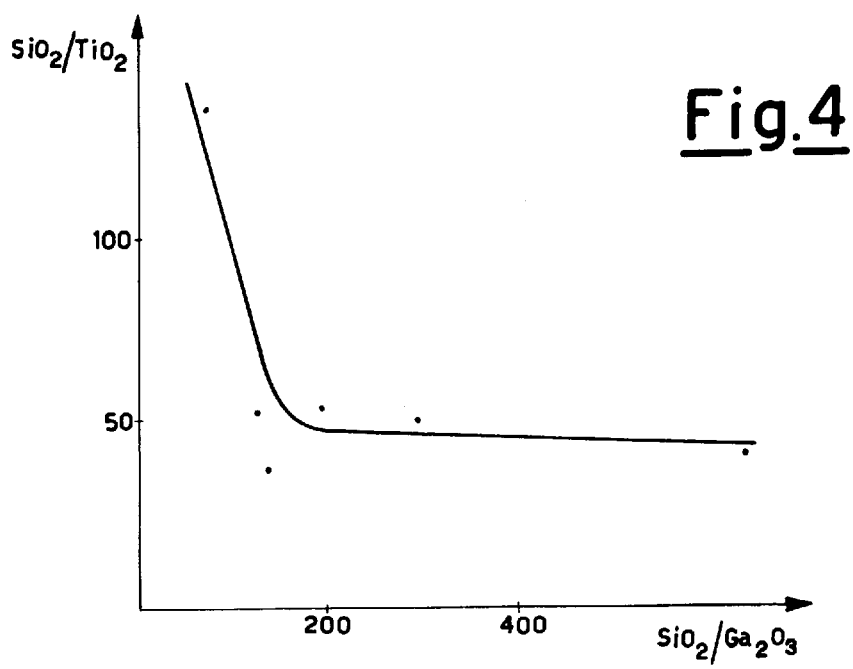
FIG. 4 shows the decrease in $SiO_2/TiO_2$ ratio with increasing $SiO_2/Ga_2O_3$ ratio.

From FIG. 4, it can be seen how the $SiO_2/TiO_2$ ratio in the obtained product decreases with increasing $SiO_2/Ga_2O_3$ ratio, until it stabilizes around a value of 40–50 for an $SiO_2/Ga_2O_3$ ratio larger than 200.

Figure 5:
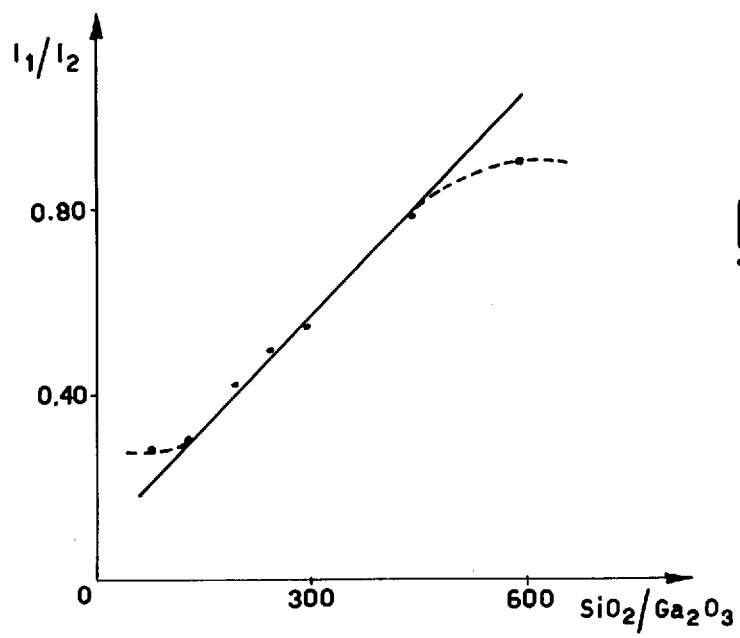
FIG. 5 shows the variation in relative intensity of the band associated with structural titanium versus $SiO_2/Ga_2O_3$ ratio.

From FIG. 5, it can be seen how in the I.R. spectrum the value varies of the relative intensity ratio between the band at 970 $cm^{-1}$ ($I_1$), attributed to structural titanium, and a silicalite band at 550 $cm^{-1}$.

Such an intensity ratio increases with increasing $SiO_2/Ga_2O_3$ ratio and this fact indicates than titanium in the crystalline lattice actually increases with decreasing gallium.

Figure 6:
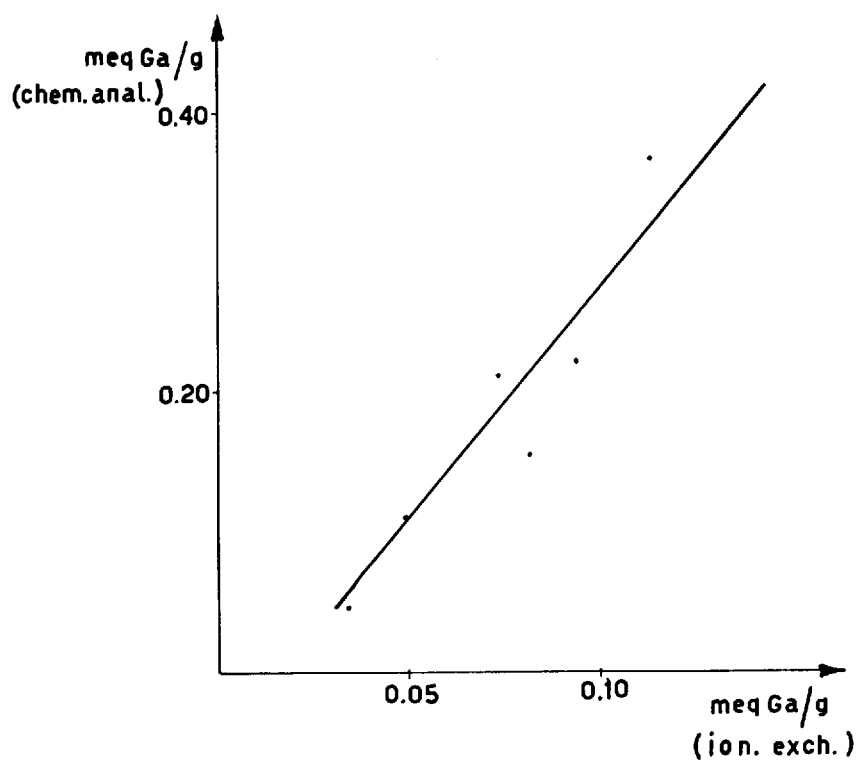
FIG. 6 shows the increase in exchange capacity of the porous material of the present invention with increase in gallium content.

From FIG. 6, it can be seen how with increasing values of gallium found in the chemical analysis, the exchange capacity of the obtained zeolite increases; this demonstrates that gallium found on chemical analysis is really structural gallium.

EXAMPLE 8

In this Examples, the preparation is shown of the catalyst of Example 1 with a bonding agent.

100 g of $Ga(NO_3)_3.8H_2O$ is dissolved in 1,050 g of $C_2H_5OH$ and the so-obtained solution is added, with mild stirring, to a solution constituted by 340.5 g of tetraethyl-titanate and 6,240 g of tetraethyl-silicate.

The so-obtained clear alcoholic solution is added, with moderate stirring, to 13,000 g of an aqueous solution at 14% of tetrapropyl-ammonium hydroxide. The mixture is maintained stirred, while being possibly heated until a single-phase, clear solution is obtained. Then, 10,500 g is added of demineralized water, with the mixture being kept stirred for a further hour. The resulting mixture is then charged to a stirred stainless-steel autoclave, and is heated, under its autogenous pressure, up to the temperature of 170° C. These conditions are maintained for 15 hours, the autoclave is then cooled and the reaction mixture is discharged. The obtained suspension is centrifuged and the solid is washed by re-dispersion and centrifuging.

550 g of tetraethyl-silicate is added with stirring to 590 g of an aqueous solution of tetrapropyl-ammonium hydroxide at 12%, and the resulting mixture is stirred for approximately 60° C. for 1 hour; then, 2,400 g of demineralized water is added, and the solution is kept stirred a further hour, while being made cool down to approximately 25° C.

Into the so-obtained clear solution, 2,050 g is carefully dispersed of the washed centrifugation cake, prepared as disclosed above. The centrifugation cake contains approximately 70% by weight of zeolite.

The resulting milky suspension is fed to a spray-dryer (NIRO-ATOMIZER; disk-atomized; inlet air temperature 300° C.; outlet air temperature 120° C.; chamber diameter 1.5 m), compact microspheres being obtained, which have an average diameter close to 20 $\mu$m.

The atomized product is heated to 550° C. under a $N_2$ atmosphere; the atmosphere is gradually turned from $N_2$ into air, and the product is maintained a further two hours at 550° C. in air.

The obtained solid has the following composition, expressed as molar ratios:

$SiO_2/Ga_2O_3=217$;
$SiO_2/TiO_2=60$.

EXAMPLE 9

4 g of catalyst according to Example 4 and 60 ml of 1-octene are charged to a glass autoclave and are then heated to the temperature of 200° C., with stirring, for 5 hours. After cooling, the suspension is filtered and the products are analysed by gas-chromatography and mass spectrometry.

1-Octene conversion: 18%

Selectivity to dimers: 95%

Selectivity to trimers: 5%

EXAMPLE 10

To a steel autoclave of 1 liter of capacity, equipped with mechanical stirrer and temperature control system, 373 g of methanol, 4 g of catalyst according to Example 8, 5.0 g of benzene (as the internal standard for gas-chromatographic analysis) and 45 g of 1-butene are charged. After adjusting the temperature at the controlled value of 22° C., to the suspension 20 ml of hydrogen peroxide at 33% (w/v) is added with intense stirring. The reaction is monitored by drawing samples for analysis and filtering them. Hydrogen peroxide is measured by iodometric titration, and the reaction products are measured by GLC, with an 1.8-meter long column packed with Ponopak PS. Forty-five minutes later the situation is as follows:

Converted $H_2O_2$: 85%

1,2-Epoxybutane : 0.0326 mol

1-Methoxy-2-hydroxybutane: 0.0795 mol 2-methoxy-1-hydroxybutane: 0.0517 mol

EXAMPLE 11

To a an autoclave of 1 liter of capacity, equipped with mechanical stirrer, temperature control system, and constant pressure control system, 193 g of methanol, and 4.0 g of catalyst according to Example 4 are charged. To a vessel connected with the autoclave, 11.2 g of $H_2O_2$ at 32% (w/w) is charged. After adjusting the temperature to the controlled value of 22° C., and pressurizing with propylene, with stirring, at 300 kPa (with this pressure being kept constant during the whole reaction time), to the suspension inside the autoclave all hydrogen peroxide is added at a time.

The reaction is monitored by drawing samples of suspension, which are filtered and analysed. Hydrogen peroxide is measured by iodometric titration, and the reaction products are measured by gas-chromatography on an 1.8-meter long column packed with Poropak PS. After 45 minutes, the situation is as follows:

Converted $H_2O_2$: 88%

Propylene oxide : $6.02\times10^{-3}$ mol

1-Methoxy-2-hydroxypropane: $52.0\times10^{-3}$ mol 2-methoxy-1-hydroxypropane: $34.6\times10^{-3}$ mol

EXAMPLE 12

To a small glass flask of 250 cc of capacity, in the following order: phenol, 99.8 g; water, 24.2 g; acetone, 18,5 g; catalyst, prepared as per Example 5, 5 g; are charged.

The reaction mixture is heated to 100° C., with stirring, and refluxing; then, under the same conditions, within a 45-minute time 15.4 g of $H_2O_2$ at 60% w/w is added dropwise.

Sixty minutes after the beginning of the addition, all $H_2O_2$ has been converted, and the reaction products are analysed by gas-chromatography.

A yield of diphenols of $$\text{yield} = \frac{\text{obtained diphenol mol}}{\text{charged } H_2O_2 \text{ mol}} \times 100 = 74.7\%$$

is obtained.

The residual amount of $H_2O_2$ is converted into pitches and $O_2$. In the obtained diphenols, the ortho/para ratio is 1.26.

replaced by cations, the material exhibiting an X-ray diffraction spectrum of:

| d | $I_{rel}$ |
|---|---|
| 11.14 ± 0.10 | vs |
| 9.99 ± 0.10 | s |
| 9.74 ± 0.10 | m |
| 6.36 ± 0.07 | mw |
| 5.99 ± 0.07 | mw |
| 4.26 ± 0.05 | mw |
| 3.86 ± 0.04 | s |
| 3.82 ± 0.04 | s |
| 3.75 ± 0.04 | s |
| 3.72 ± 0.04 | s |
| 3.65 ± 0.04 | m |
| 3.05 ± 0.02 | mw |
| 2.99 ± 0.02 | mw | wherein d is the interplanar distance, expressed as Å, and $I_{rel}$ is the relative intensity, wherein vs means very strong, s means strong, m means medium, and mw means medium weak, and the material exhibiting an I.R. spectrum having at least the following bands:

| wn | $I_{rel}$ |
|---|---|
| 1220–1230 | w |
| 1080–1110 | s |
| 965–975 | mw |
| 795–805 | mw |
| 550–560 | m |
| 450–470 | ms | wherein wn is the wave number, as $cm^{-1}$, and $I_{rel}$ is the relative intensity, wherein s means strong, ms means medium-strong, m means medium, mw means medium weak and w means weak, said synthetic, crystalline, porous material being produced by reacting under hydrothermal conditions a silicon derivative, a titanium derivative, a gallium derivative, a nitrogenous organic base and one or more alkali or alkali-earth metal salts and/or hydroxides having an alkali or alkali-earth metal cation M with a $SiO_2/Ga_2O_3$ molar ratio of the reactants larger than 100, a $SiO_2/TiO_2$ molar ratio of the reactants larger than 5 and a $M/SiO_2$ molar ratio of the reactants smaller than 0.1 or equal to zero wherein M is an alkali and/or alkali-earth metal cation.

TABLE 1

| | Composition of the Reaction Mixture | | | | Product Composition | |
|---|---|---|---|---|---|---|
| Example | $SiO_2/TiO_2$ | $SiO_2/Ga_2O_3$ | $TPA^+/SiO_2$ | $H_2O/SiO_2$ | $SiO_2/TiO_2$ | $SiO_2/Ga_2O_3$ |
| 1 | 20 | 250 | 0.3 | 40 | 54.2 | 195.5 |
| 2 | 20 | 50 | 0.3 | 40 | Not crystallized | |
| 3 | 20 | 80 | 0.3 | 40 | 135.5 | 79.2 |
| 4 | 20 | 130 | 0.3 | 40 | 53.3 | 128.8 |
| 5 | 20 | 300 | 0.3 | 40 | 50.9 | 294.1 |
| 6 | 20 | 600 | 0.3 | 40 | 43.5 | 641.7 |

We claim:

1. Synthetic, crystalline, porous material comprising oxides of silicon, titanium, and gallium, having the following formula, in its calcinated and anhydrous state:

$$pHGaO_2 \cdot qTiO_2 \cdot SiO_2$$

wherein p is a value larger than zero and smaller than or equal to 0.050, q is a value larger than 0 and smaller than or equal to 0.025, and the $H^+$ of $HGaO_2$ can be at least partially replaced by cations, 2. The product according to claim 1 wherein M is a sodium cation.

3. The product according to claim 1 wherein a $H_2O/SiO_2$ ratio of the reactants is from 10 to 100.

4. The product according to claim 1, wherein the $SiO_2/Ga_2O_3$ molar ratio is from 150 to 600, the $SiO_2/TiO_2$ molar ratio is from 15 to 25, the $H_2O/SiO_2$ ratio is from 30 to 50, and the $M/SiO_2$ ratio is about equal to zero.

5. The product according to Claim 1, wherein the silicon derivative is selected from silica gel, silica sol and alkylsilicates, the titanium derivative is selected from titanium salts and organic titanium derivatives, and the gallium derivative is selected from gallium salts.

6. The product according to claim 5, wherein the alkyl-silicate is tetraethyl-silicate.

7. The product according to claim 5, wherein the titanium salts are titanium halides.

8. The product according to claim 5, wherein the organic titanium derivatives are alkyl-titanates.

9. The product according to claim 5, wherein the alkyl-titanate is tetraethyl-titanate.

10. The product according to claim 5, wherein the gallium salts are selected from gallium halides, nitrates and hydroxides.

11. The product according to claim 1, wherein the nitrogenous base is alkyl-ammonium hydroxide.

12. The product according to claim 1, wherein the alkyl-aluminum hydroxide is tetrapropyl-ammonium hydroxide.

13. The product according to claim 1, wherein the reaction is conducted at a temperature from 100° to 200° C., at a pH from 9 to 14, and for a time from 1 hour to 5 days.

14. The product according to claim 10, wherein the $TPA^+/SiO_2$ molar ratio of the reactants is from 0.1 to 1.

15. The product according to claim 4, 6, 9, 12 or 14, wherein the $TPA^+/SiO_2$ molar ratio is from 0.2 to 0.4.

* * * * *